United States Patent [19]

Burrows et al.

[11] Patent Number: 4,987,227
[45] Date of Patent: Jan. 22, 1991

[54] POLYAZAMACROCYCLES AND THEIR METAL COMPLEXES

[75] Inventors: Cynthia Burrows; Heungsik Yoon, both of Stony Brook, N.Y.; Thomas R. Wagler, Chatham, N.J.

[73] Assignee: The Research Foundation of State University of New York, Albany, N.Y.

[21] Appl. No.: 484,102

[22] Filed: Feb. 23, 1990

Related U.S. Application Data

[63] Continuation-in-part of Ser. No. 261,032, Oct. 21, 1988, abandoned.

[51] Int. Cl.$^5$ ............................................. C07D 257/02
[52] U.S. Cl. .................................... 540/452; 534/10; 534/11; 534/12; 534/13; 534/14; 534/15; 534/16; 540/460; 540/465; 540/471; 540/475
[58] Field of Search .................... 534/10, 11, 12, 13, 534/14, 15, 16; 540/452, 460, 465, 471, 475

[56] References Cited

FOREIGN PATENT DOCUMENTS 184068 9/1985 Japan .

OTHER PUBLICATIONS

Chemical Abstracts, vol. 100 (1984) 77303s.
Busch, Acc. Chem. Res. 1978, 11, 392–400.
Bhattacharya, et al., Inorg. Chem. 1986, 25, 3448–3452.
Kimura et al., Inorg. Chem. 1984, 23, 4181–4188.
Kimura, et al., J. Am. Chem. Soc. 1984, 106, 5497–5505.
Kushi, et al., J. Chem. Soc., Chem. Commun. 1985, 216–218.
Machida, et al., Inorg. Chem. 1986, 25, 3461–3466.
Kimura, et al., J. Am. Chem. Soc. 1988, 110, 3679–3680.
Kimura, Pure Appl. Chem. 1986, 58, 1461–1466.
Kimura, et al., Ibid. 1986, 25, 3883–3886.
Kimura, et al., J. Chem. Soc., Chem. Commun. 1986, 1158–1159.
Kimura, et al., Ibid. 1986, 1322–1323.
Kimura, et al., Ibid. 1987, 1712–1714.
Kimura, et al., Inorg. Chem. 1987, 26, 2975–2983.
Kimura, et al., J. Am. Chem. Soc. 1987, 109, 5528–5529.
Kaden, Topics Curr. Chem. 1984, 121, 157–179.
Korybut-Daszkiewicz, Chem. Soc., Chem. Commun. 1985, 192–193.
Barefield, et al., Inorg. Chem. 1986, 25, 4663–4668.
Pallavicini, et al., J. Am. Chem. Soc. 1987, 109, 5139–5144.
Morphy, et al., Chem. Soc., Chem. Commun. 1988, 156–158.
Wagler, et al., J. Chem. Soc., Chem. Commun., 1987, 277–278.
Tabushi, et al., Tetrahedron Lett. 1977, 18, 1049–1052.
Koola, et al., Inorg. Chem. 1987, 26, 908–916.
Yoon, et al., J. Am. Chem. Soc. 1988, 110, 4087–4089.
Kinneary, et al., Tetrahedron Lett. 1988, 29, 877–880.
Kinneary, et al., J. Am. Chem. Soc. 1988, 110, 1624–1629.
Guilmet, et al. Tetrahedron Lett. 1980, 21, 4449–4450.
Guilmet, et al., Ibid, 1982, 23, 2449–2452.
Guilmet, et al., Nouv. J. Chim. 1982, 6, 511–513.
Collman, et al., Proc. Natl. Acad. Sci. U.S.A., 1983, 80, 7039–7041.
Meunier, et al., J. Am. Chem. Soc. 1984, 6668–6676.
Collman, et al., J. Am. Chem. Soc. 1985, 107, 2000–2005.
Montanari, et al., I. Org. Chem. 1985, 50, 4888–4893.
Banfi, et al., Gazz. Chim. Ital. 1987, 117, 689–693.
Banfi, et al., J. Org. Chem. 1988, 2863–2866.
Montanari, et al. Pure & Appl. Chem. 1989, 9, 1631–1636.
Harrington, et al., Inorg. Chem. 1973, 12, 168–178.
Poddar, et al., J. Indian Chem. Soc., 1963, 6, 489–490.
Pfeiffer, et al., Ann. 1933, 503, 84–130.

*Primary Examiner*—Richard L. Raymond
*Attorney, Agent, or Firm*—Hoffmann & Baron

[57] ABSTRACT

A 13 or 14 member macrocyclic compound having the following ring nucleus:

(Abstract continued on next page.)

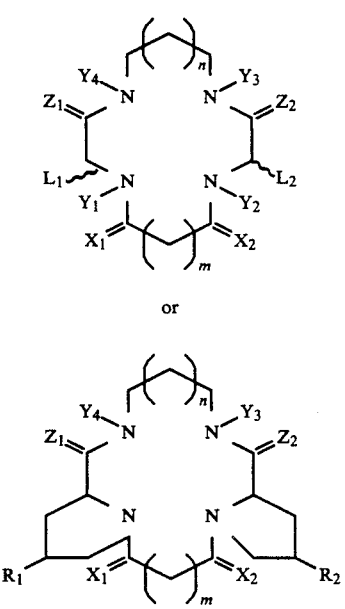

wherein:

IA

IB n=0 or 1;
m=0 or 1;
n+m>0;

$X_1$, $X_2$, $Z_1$ and $Z_2$ independently represent $H_2$ or O; and $Y_1$, $Y_2$, $Y_3$ and $Y_4$ independently represent H, lower alkyl or $CH_2COOH$: and $L_1$ and $L_2$ independently represent side chains of alpha amino acids, except that $L_1$ and $L_2$ do not both represent H; and $R_1$ and $R_2$ independently represent H or OH forms stable complexes with transition metal ions that may be used as catalysts for oxidizing alkenes to epoxides with oxidizing agents.

A method is also provided for oxidizing alkenes to epoxides by treating the alkene with a transition metal ion complex which includes the 13 or 14 member macrocyclic compound of the invention, a cyclam or a Schiff base complex and peroxymonosulfate ion or hypochlorite ion in a two phase system comprising a phase transfer catalyst, a water phase having a pH about 6 to about 14 and an inorganic solvent phase in which the complex is sufficiently soluble.

25 Claims, 12 Drawing Sheets

POLYAZAMACROCYCLES AND THEIR METAL COMPLEXES

This work was supported by grants from the National Institutes of Health (GM-34841) and the National Science Foundation (CHE-8706616).

This is a continuation-in-part of copending application Ser. No. 261,032 filed on Oct. 21, 1988 now abandoned.

The present invention is directed to transition metal-catalyzed transfer of oxygen atoms to organic substrates. In addition, the invention is directed to substituted polyazamacrocycles having 13 and 14 membered rings that are easily prepared from amino acids, and the transition metal complexes of such polyazamacrocycles. The polyazamacrocycle complexes or Schiff base complexes may be used in the rapid conversion of alkenes to epoxides at a high turnover rate under certain novel phase transfer conditions.

Polyhetero atom macrocycles have been extensively studied, especially with respect to their ability to form complexes with metal ions. A good example of such polyhetero macrocycles are the polyethers, which readily form complexes with alkali and alkaline earth metals.

Polyazamacrocycles have been investigated due to their ability to form complexes with transition metal ions. A typical polyazamacrocycle capable of complexing transition metal ions is 1,4,8,11-tetraazacyclotetradecane (cyclam). Cyclam has structure 1. The ability of cyclam and its derivatives to form stable complexes with cobalt, nickel, copper and other metal ions and to stabilize high oxidation states of these metals has recently been studied (Busch, Acc. Chem. Res. 11, 392–400 (1978)).

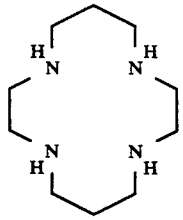

More recently, 1,4,8,11-tetraazacyclotetradecane-5,7-dione (dioxocyclam) has been developed and its ability to form complexes with a limited number of metal ions studied. These complexes involve the coordination of the metal ions to a deprotonated ligand. The structure of dioxocyclam is shown as structure 2.

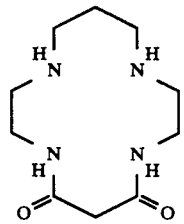

and the structure of the nickel complex of dioxocyclam is shown as structure 3.

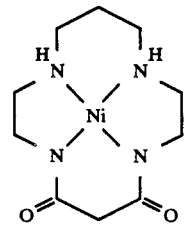

In addition to the utilities mentioned above, certain complexes of transition metal ions, such as the square planar complexes of $Ni^{2+}$, have been shown to catalyze the transfer of oxygen atoms to alkenes. Epoxides are the principal products of these reactions. Ligands used in the complexes for these reactions have included cyclam, N,N'-ethylene-bis(salicylideneamine), also known as salen and trans-1,2-diaminocyclohexane, also known as salophen. The structure of Ni(salen) is shown as structure 4.

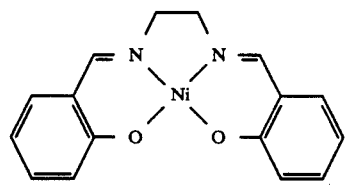

The structure of Ni(salophen) is shown as structure 5.

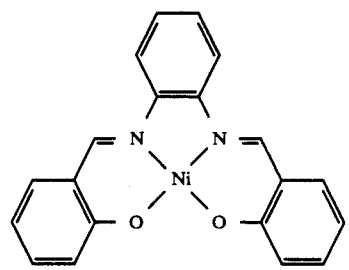

Relatively strong oxidizing agents, such as iodosylbenzene and hypochlorite ion, are required to oxidize alkenes to epoxides under these conditions. The success of the reactions depend in part on the solubility of the alkene, the oxidizing agent and the catalytic metal complex in the solvent in which the reaction is conducted. The problem of finding a suitable reaction medium was solved by Yoon and Burrows for the oxidation of alkenes with sodium hypochlorite and salen by conducting the reaction under phase transfer conditions; these researchers also described catalysis of alkene oxidation by structures 1, 4 and 5 using NaOCl at pH 13 under phase transfer conditions (Yoon and Burrows, J. Am. Chem. Soc. 110, 4087–4089 (1988)). The article at J. Am. Chem. Soc. 110, 4087–4089 (1988) is incorporated by reference herein in its entirety. The catalyst for phase transfer reactions may also be manganese porphyrins (Meunier et al., J. Am. Chem. Soc., 106, 6668–6676 (1984)).

Complexes of Schiff base derivatives such as Ni (salen) were used for olefin expoxidation with iodosylbenzene in very large excess as the terminal oxidant by Koola et al., Inorg Chem. 26, 908–16 (1987).

It has now been discovered that the rate of epoxidation when using the cyclam, dioxocyclam or Schiff base transition metal complexes is dramatically influenced by pH.

These reactions also generally suffer from a lack of flexibility in adjusting the solubility of the metal ion complex in the organic reaction media useful for organic reactions. Various substituent groups including alkyl groups have been introduced into the three carbon bridge of the cyclam and dioxocyclam ring systems. See Kimura, et al., Inorg. Chem. 1984, 23, 4181–4188; Kimura, et al., J. Am. Chem. Soc. 1984, 106, 5497–5505; Kushi, et al., J. Chem. Soc., Chem. Commun. 1985, 216–218; Machida, et al., Inorg. Chem. 1986, 25, 3461–3466; Kimura, et al., J. Am. Chem. Soc. 1988, 110, 3679–3680 and Tabushi, et al., Tetrahedron Lett. 1977, 18, 1049–1052. Such compounds, however, do not always provide the necessary flexibility and are not always sufficiently easy to make in order to be practical for commercial purposes.

Moreover, a substituent in the two carbon bridge of the cyclam and dioxocyclam ring system would be closer to the site of the reaction, which is believed to occur when the complexed metal transports an oxygen atom to the alkene. When the substituents in the two carbon bridge are on chiral carbon atoms, the possibility exists that a resulting epoxide also having a chiral carbon atom would be optically active. Such asymmetric induction would be useful in the synthesis of optically active compounds.

There is, therefore, a need for a new class of easily synthesized polyazamacrocycles having a range of solubilities in media suitable for the oxidation of alkenes to epoxides. It would, furthermore, be desirable for such compounds to have substituents at an asymmetric carbon atom.

OBJECTS OF THE INVENTION

It is an object of the invention to provide rapid chemical reactions for oxidizing alkenes to epoxides in high yield.

It is an additional object of the present invention to provide 13 and 14 member polyazamacrocycles capable of forming stable complexes with transition metal ions.

It is a further object of the present invention to provide complexes of 13 and 14 member rings and transition metal ions capable of oxidizing alkenes to epoxides.

It is also an object of the present invention to provide 13 and 14 member polyazamacrocycles capable of forming complexes with transition metal ions for sequestration, biomimetic catalysis and biomedical applications.

SUMMARY OF THE INVENTION

These and other objectives as will be apparent to those with ordinary skill in the art have been achieved by providing a 13 or 14 member macrocyclic ring nucleus having the structure:

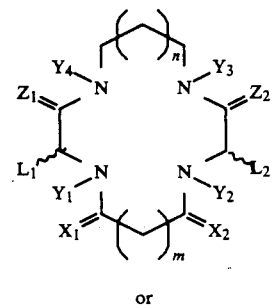

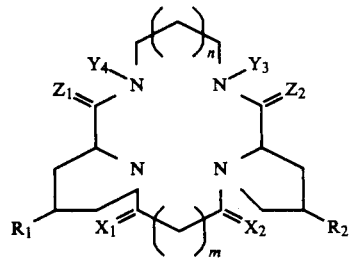

wherein:
n=0 or 1;
m=0 or 1;
n+m>0;
$X_1$, $X_2$, $Z_1$ and $Z_2$ independently represent $H_2$ or O;
$Y_1$, $Y_2$, $Y_3$ and $Y_4$ independently represent H, lower alkyl or $CH_2COOH$;
$L_1$ and $L_2$ represent side chains derived from alpha amino acids, except that $L_1$ and $L_2$ do not both represent H; and
$R_1$ and $R_2$ independently represent H or OH.

The ring nucleus having structure IA or IB forms stable complexes with transition metals, and may be used to oxidize alkenes to epoxides.

In a method for oxidizing alkenes to epoxides, the alkene is treated with a transition metal complex and an oxidizing agent in a two phase system including a phase transfer catalyst. A water phase has a pH less than 12.9, and the system also includes an organic solvent phase in which the complex is sufficiently soluble.

For a better understanding of the present invention, together with other and further objects, reference is made to the following description, taken together with the accompanying drawing, and its scope will be pointed out in the appended claims.

DETAILED DESCRIPTION OF THE INVENTION

The Macrocyclic Ring Compounds

Figure 1:
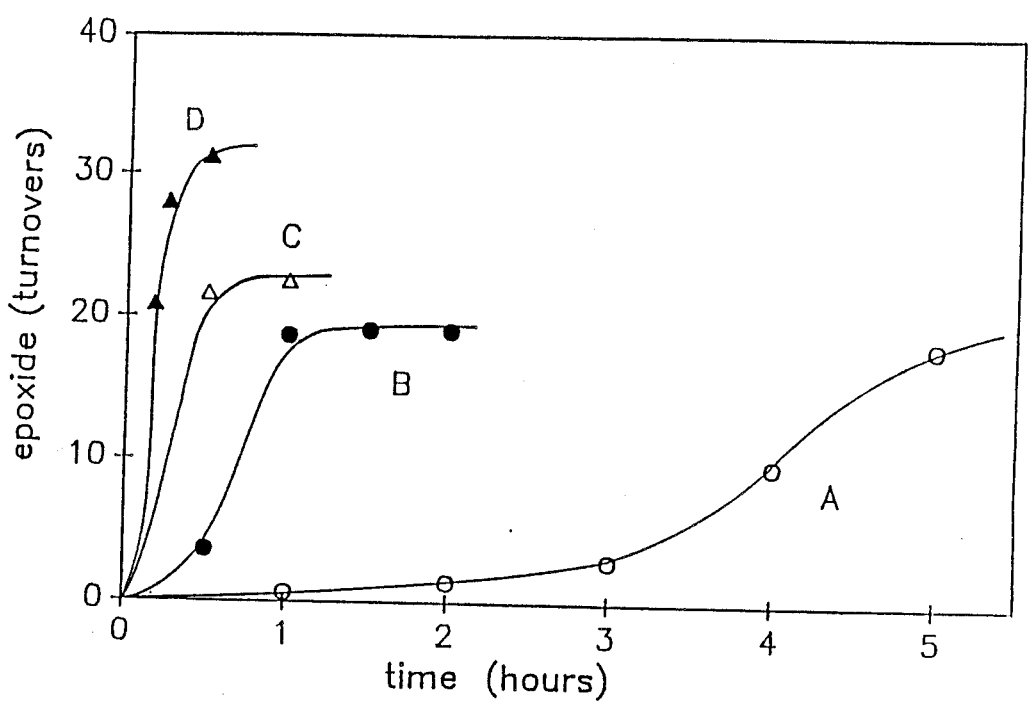
FIG. 1 is a graph showing the effect of pH and additives on the turnover rate of $Ni^{II}$(salen)-catalyzed epoxidation of styrene.

The compounds represented by structure IA and IB are characterized by their ability to form stable complexes with transition metals. Stable complexes are those having measurable lifetimes at room temperature in water or common organic solvents.

The ability of IA and IB to form stable complexes results from the relative positions of the nitrogen atoms. The rest of the ring nucleus consists of carbon atoms that may be thought of as collectively forming a scaffold for maintaining the proper position of the nitrogen atoms.

Substituents on the atoms of the ring nucleus affect the properties of the compounds, such as their solubility in various solvents and the stability of the complex they form with transition metals. The only substituents that are critical to the present invention are $L_1$ and $L_2$. The ring carbon and nitrogen atoms other than the carbon atoms that bear $L_1$ and $L_2$ are normally substituted with sufficient hydrogen atoms to form a stable compound. It should be appreciated, however, that any of the positions, whether or not so indicated in IA and IB, may be substituted with any other group and still do substantially the same thing in substantially the same way to accomplish the same result and are, therefore, to be considered equivalent to positions bearing hydrogen atoms as substituents for the purpose of determining the scope of the present invention.

For example, some of the positions shown in structures IA and IB do not appear to have substituents other than hydrogen. Nevertheless, even these positions may be substituted by any organic or inorganic group without significantly affecting the ability of the compound to form a complex with transition metals.

Accordingly, any one or more of these positions may be substituted by an inorganic substituent, such as a doubly bonded oxygen, i.e., carbonyl, or a singly bonded oxygen i.e., hydroxy. Some additional inorganic groups include, for example, amino, thio, halo, i.e., F, Cl, Br, and I, etc.

Organic substituents include, for example, alkyl, aryl, alkylaryl and arylalkyl. The alkyl groups may be branched or unbranched and contain 20 carbon atoms or less, preferably 8 carbon atoms or less, and more preferably 4 carbon atoms or less. Some typical examples of alkyl groups include methyl, ethyl, n-propyl, isopropyl, n-butyl, sec-butyl, tert-butyl, isobutyl, and octyl. The alkyl groups may, in whole or in part, be in the form of rings such as cyclopentyl, cyclohexyl, cycloheptyl and cyclohexylmethyl. The cyclic groups described above may be further substituted with inorganic, alkyl, or aryl groups. Any of the alkyl groups described above may have one or more double or triple bond. Moreover, any of the carbon atoms of the alkyl groups may be separated from each other or from the ring nucleus with groups such as carbonyl, oxycarbonyl, oxy, amino, thio, etc. Alkyl groups may also terminate with groups such as halo, hydroxy, amino, carboxy, etc.

Aryl substituents are typically phenyl, but may also be any other aryl group such as, for example, pyrrolyl, furanyl, thiophenyl, pyridyl, thiazolyl, etc. The aryl group may, further, be substituted by an inorganic, alkyl, or other aryl group.

The alkylaryl and arylalkyl groups may be any combination of alkyl and aryl groups. These groups may be further substituted.

In structures IA and IB, n and m independently, represent 0 or 1 except that n and m do not both represent 0. Accordingly, the macrocyclic ring nucleus of structures IA and IB has 13 or 14 members. The preferred ring size depends on the diameter of the ion being complexed.

$X_1$, $X_2$, $Z_1$ and $Z_2$ independently represent two hydrogen atoms or a doubly bonded oxygen atom. As mentioned above, either or both of the hydrogen atoms may be substituted by any inorganic or organic groups. Preferably, $X_1$ and $X_2$ both represent doubly bonded oxygen while $Z_1$ and $Z_2$ represent two singly bonded hydrogen atoms i.e., $H_2$.

$Y_1$, $Y_2$, $Y_3$ and $Y_4$, independently represent hydrogen or any other inorganic or organic group, especially a group that will stabilize a complex with a transition metal cation. For example, $Y_1$, $Y_2$, $Y_3$ and $Y_4$ may, independently, represent alkyl, especially lower alkyl, i.e., $C_1$–$C_4$. A group that is particularly advantageous on the ring nitrogen atoms is $CH_2COOH$, which tends to enhance the association of metal ions to polyamine ligands.

$L_1$ and $L_2$ independently represent a group (L) derived from an alpha amino acid, $LCH(NH_2)CO_2H$. The alpha amino acid may be naturally occurring or synthetic. Some examples of synthetic alpha amino acids include, for example, phenylglycine ($L_1$ and/or $L_2$=phenyl) and 2-amino-3,3-dimethylbutanoic acid ($L_1$ and $L_2$=tert-butyl). Some examples of naturally occurring amino acids include, for example, those shown in the table below:

| Amino Acid | Natural Amino Acids | |
|---|---|---|
| | Abbreviation | $L_1$ and/or $L_2$ |
| (+)-Alanine | Ala | $CH_3$ |
| (+)-Arginine | Arg | $\underset{+NH_2}{H_2NC{\overset{\parallel}{N}}HCH_2CH_2CH_2}$ |
| (−)-Asparagine | Asp(NH$_2$) | $H_2NCOCH_2$ |
| (+)-Aspartic acid | Asp | $HOOCCH_2$ |
| (−)-Cysteine | CySH | $HSCH_2$ |
| (−)-Cystine | CyS-SCy | $\underset{+NH_3}{-OOCCHCH_2S-SCH_2}$ |
| (+)-3,5-Dibromotyrosine | | 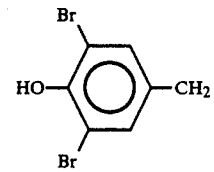 |

-continued

| Amino Acid | Natural Amino Acids Abbreviation | $L_1$ and/or $L_2$ |
|---|---|---|
| (+)-3,5-Diiodotyrosine | | HO–(C$_6$H$_2$I$_2$)–CH$_2$ (3,5-diiodo-4-hydroxyphenyl-CH$_2$) |
| (+)-Glutamic acid | Glu | HOOCCH$_2$CH$_2$ |
| (+)-Glutamine | Glu(NH$_2$) | H$_2$NCOCH$_2$CH$_2$ |
| Glycine | Gly | H |
| (−)-Histidine | His | imidazolyl-CH$_2$ |
| (−)-Hydroxylysine | Hylys | H$_2$NCH$_2$CHCH$_2$CH$_2$ with OH on middle CH |
| (+)-Isoleucine | Ileu | CH$_3$CH$_2$CH(CH$_3$) |
| (−)-Leucine | Leu | (CH$_3$)$_2$CHCH$_2$ |
| (+)-Lysine | Lys | H$_2$NCH$_2$CH$_2$CH$_2$CH$_2$ |
| (−)-Methionine | Met | CH$_3$SCH$_2$CH$_2$ |
| Ornithine | | NH$_2$CH$_2$CH$_2$CH$_2$ |
| (−)-Phenylalanine | Phe | C$_6$H$_5$–CH$_2$ |
| (−)-Serine | Ser | HOCH$_2$ |
| (−)-Threonine | Thr | CH$_3$CH(OH) |
| (+)-Thyroxine | | HO–(C$_6$H$_2$I$_2$)–O–(C$_6$H$_2$I$_2$)–CH$_2$ |
| (−)-Tryptophane | Try | indolyl-CH$_2$ |
| (−)-Tyrosine | Tyr | HO–C$_6$H$_4$–CH$_2$ |
| (+)-Valine | Val | (CH$_3$)$_2$CH |

When the amino acid is hydroxyproline or proline, the polyazamacrocycle has structure IB wherein $R_1$ and $R_2$ independently represent H or OH, and n, m, $X_1$, $X_2$, $Z_1$, $Z_2$, $Y_3$ and $Y_4$ have the same meaning as described above. The groups of the other natural amino acids have structure IA.

In order to benefit from the versatility of the $L_1$ and $L_2$ groups, $L_1$ and $L_2$ in the polyazamacrocycles of the present invention should not both be H. Preferably, when one of $L_1$ or $L_2$ is H, the other is not CH$_3$.

As will be shown below, compounds having the ring nucleus shown in structure IA and IB may be easily synthesized from amino acids. The synthesis does not affect the stereochemical integrity of the alpha carbon atoms of the amino acids, which, in nature, has the L or, in Cahn-Ingold-Prelog terminology, S configuration.

Accordingly, the configuration at positions 3 and 9 when m represents 1 and positions 3 and 8 when m represents 0 is the same as that of the alpha carbon atom of the amino acid from which the macrocycle is made. In the case of a natural amino acid, these configurations are S, and structure IA may more precisely be drawn as structure IC.

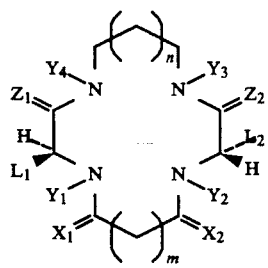

IC wherein m, n, $X_1$, $X_2$, $Y_1$, $Y_2$, $Y_3$, $Y_4$, $Z_1$, $Z_2$, $L_1$ and $L_2$ have the same meaning as for structure IA.

It should be noted that the configuration of the alpha carbon atom of the amino acid used as the starting material does not change when the amino acid is converted to the corresponding macrocycle. The R or S designation of the carbon atom in the macrocycle corresponding to the alpha carbon atom of the amino acid may change depending on the various substituents in IC. $Z_1$ and $Z_2$ will be particularly influential in this regard.

It should be further noted that where one or both of the amino acids used as the starting compound is proline, $L_1$ and $Y_1$ and/or $L_2$ and $Y_2$ in structures IA and IC are joined together in a 5 membered ring. In the case of hydroxyproline, the 3 position of the 5 member ring is substituted with a hydroxy group.

The synthesis of the compounds having structure IA or IB may also start with amino acids having the D (or R) configuration. Under these circumstances, the configuration of the carbon atoms at positions 3 and 9 when m represents 1 and positions 3 and 8 when m represents 0 will be R (assuming $Z_1$ and $Z_2$ represent doubly bonded oxygen).

When positions 3 and 9 when m represents 1 and positions 3 and 8 when m represents 0 have the same configuration, $L_1$ and $L_2$ will be oriented in an anti fashion with respect to each other on the macrocyclic ring. When anti $L_1$ and $L_2$ groups are identical in IA and IB, the two faces of the ring are equivalent and the molecule has $C_2$ symmetry.

The carbon atoms bearing $L_1$ and $L_2$ may also have different configurations. This will occur when one of $L_1$ or $L_2$ is from an amino acid with the S configuration while the other of $L_1$ or $L_2$ is from an amino acid with the R configuration. Under such circumstances the compound will be a meso compound when $L_1$ and $L_2$ are identical.

The Complexes

The compounds of the present invention form stable complexes with transition metal ions. For the purpose of this specification, transition metals are to be understood as including metals having partly filled d or f shells in any of their commonly occurring oxidation states. Accordingly, transition metals include the first transition series, which consists of Sc, Ti, V, Cr, Mn, Fe, Co, Ni, and Cu, as well as the second transition series, which consists of Y, Zr, Nb, Mo, Tc, Ru, Rh, Pd, and Ag. The transition metals in accordance with the above definition further includes the lanthanide series, which consists of La, Ce, Pr, Nd, Pm, Sm, Eu, Gd, Tb, Dy, Ho, Er, Tm, Yb, and Lu, the third transition series, which consists of Hf, Ta, W, Re, Os, Ir, Pt, and Au, and the actinide series, which consists of Ac, Th, Pa, U, Np, Pu, Am, Cm, Bk, Cf, Es, Fm, Md, No, and Lw. The most useful transition metal ions are those of the first transition series, the second transition series, the lanthanide series and the third transition series.

The complexes are formed by contacting a salt of the metal ion with the polyazamacrocycles in a suitable solvent such as, for example, water and methanol. Progress of the complexation is easily followed visually or spectrophotometrically. Depending upon reaction conditions such as the ligand, the metal, the pH, and the solvent, the complexation reaction may occur rapidly at room temperature, or may require heating.

Some examples of metal ions capable of forming complexes in accordance with the present invention include $Ni^{2+}$, $Co^{2+}$, $Cu^{2+}$, $Mn^{2+}$, and $Gd^{3+}$, $Pt^{2+}$ and $Pd^{2+}$. Some examples of salts capable of forming such complexes include $NiCl_2$, $Ni(OAc)_2$, $Cu(OAc_2)$, $Pd(OAc)_2$ and $Pt(OAC)_2$.

Under some conditions, the complex that is formed is deprotonated. Deprotonation is most likely to occur with hydrogens that are attached to amido nitrogen atoms. Thus, deprotonation may occur in complexes of structure IA when $Y_1$ represents H and $X_1$ represents 0; when $Y_2$ represents H and $X_2$ represents 0; when $Y_3$ represents H and $Z_2$ represents 0; and when $Y_4$ represents H and $Z_1$ represents 0. For example, when nickel acetate is warmed with a compound having formula IA wherein n and m both represent 1; $X_1$ and $X_2$ both represent 0; $Y_1$, $Y_2$, $Y_3$, $Y_4$, $Z_1$ and $Z_2$ all represent H, the following complex is formed:

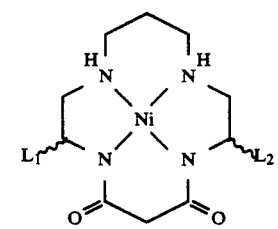

II

Complexes such as II between a doubly positive metal ion and a di-deprotonated ligand are particularly stable, since they are neutral molecules. Such di-deprotonated complexes are particularly suitable for catalyzing oxidation reactions of alkenes with oxidizing agents such as hypochlorite ion, since such di-deprotonated complexes are square planar. Square planar complexes are believed to be more effective oxidation catalysts than complexes having other geometries.

Utility

The compounds having formula IA and IB are useful in the sequestration of transition metal ions. Therefore, these compounds may be used in the qualitative and quantitative assays of transition metal ions. (For example, see Kaden, Topics in Current Chemistry, 121, 157-180 (1984)). The complexes formed when compounds IA and IB sequester transition metal ions are, further, useful in biomimetic catalysis (Kinneary et al., Tetrahedron letters, 29, 877 (1988)) and in biomedical applications (Morphy et al., J. Chem. Soc., Chem. Commun., 156 (1988)).

Oxidations

The transition metal complexes of the present invention are particularly useful in the oxidation of alkenes to epoxides with a variety of water-soluble oxidizing agents under phase transfer conditions. The oxidations may also utilize Schiff base complexes such as a salen or a salophen. Salen complexes may be prepared using the method of Poddar et al., J. Indian Chem. Soc. 40, 489–490 (1963).

Some examples of oxidizing agents include peroxymonosulfate salts and hypochlorite salts. The preferred peroxymonosulfate salt is potassium peroxymonosulfate, which is commercially available under the trademark OXONE. Some examples of hypochlorite salts include lithium, sodium and potassium hypochlorite. Any transition metal capable of catalyzing the oxidation may be used in the complex. The complexes of $Ni^{2+}$, $Cu^{2+}$, $Co^{2+}$, $Pd^{2+}$ and $Pt^{2+}$ are preferred. $Ni^{2+}$ is especialy preferred.

The oxidizing agent is dissolved in water and the alkene to be oxidized is dissolved in a suitable organic solvent, for example, $CH_2Cl_2$, $CHCl_3$ or toluene. A phase transfer catalyst is added to the system in order to deliver the water soluble oxidizing agent into the organic phase.

The complexes of the present invention are particularly suitable for catalyzing oxidation reactions under such conditions, since complexes having various $L_1$ and $L_2$ groups may easily be synthesized (see below). Having a large selection of various $L_1$ and $L_2$ groups provides flexibility in tailoring an oxidation catalyst with the right solubilities in the two phases. The temperature at which the oxidation reaction is conducted is not critical, and may conveniently be varied between 0° C. and the boiling point of the organic solvent. Preferably, the reaction may be conducted at room temperature. The progress of the reaction may be monitored by chromatography or spectrophotometry.

The rate of oxidation is dramatically influenced by the pH. Lowering the pH accelerates the epoxidations. The pH of the reaction may vary from about 6 to about 14, more preferably below 12.5 and most preferably between 9 and 10.5 when hypochlorite is the oxidizing agent and between 6 and 9, preferably between 7 and 8 when peroxymonosulfate is the oxidizing agent. On an overall basis, pH ranges may be described as from about 6 to about 12.9, with 8.5 to 12 preferred and 8 to 11 most preferred. The rate of oxidation and product yield are influenced by the pH and also by the presence of weak organic acids soluble in the organic phase, for example uncomplexed Schiff bases and certain salicylaldehydes. Other useful weak acids are, for example, phenols which are more soluble in dichloromethane than in water and which have $pK_a$ values less than about 8. The organic acid may be added in an amount of from about 0.001 to about 0.5 moles of organic acid per mole of alkene, preferably from about 0.003 to about 0.05. The concentration of the alkene is not critical and may vary between wide limits. For example, the reaction may conveniently be conducted in an alkene concentration between 0.01 and 1M, preferably between 0.2 and 0.6M.

The concentration of the hypochlorite salt in the aqueous phase is also not critical and depends in part upon the concentration of the alkene concentration in the organic phase. The ratio of equivalents of hypochlorite ion to alkene may vary between 2:1 and 10:1, preferably between 4:1 and 5:1. Preferably the hypochlorite is slowly added to the reaction mixture at a rate of from about 0.01 to about 10 equivalents of hypochlorite ion per alkene equivalent per minute, more preferably 0.4 to 2 equivalents per minute.

The ratio of equivalents of the transition metal complex to that of the alkene substrate is also not critical, and may vary between, for example, 1:10 and 1:10,000, preferably between 1:100 and 1:4000.

Some suitable phase transfer catalysts include, for example, benzyltrimethylammonium salts, such as the halides, and especially the bromide. The concentration of the phase transfer catalyst is also not critical and may vary widely. Some suitable phase transfer catalyst concentrations include 0.005–0.05M, preferably 0.01–0.03M.

II a–d were prepared in order to test various complexes as catalysts under phase transfer conditions:

a: $L_1$ and $L_2 = CH_2Ph$
b: $L_1$ and $L_2 = CH_2CH(CH_3)_2$
c: $L_1$ and $L_2 = CH(CH_3)_2$
d: $L_1$ and $L_2 = H$ Standard reaction conditions involved treatment with vigorous stirring of 1.7 mmol trans-beta-methylstyrene, 0.04 mmol of the appropriate $Ni^{2+}$ catalyst (IIa–d) and 0.08 mmol $PhCH_2NMe_3^+$ $Br^-$ (phase transfer catalyst) dissolved in 5 ml $CH_2Cl_2$ with 10 ml 0.77M aqueous NaOCl (pH 12–13). Reactions were carried out at room temperature. Periodically removed aliquots of the organic layer were monitored by gas chromatography. The yields of oxidation products obtained are listed in Table I below.

TABLE I

| | Percent Product Yields from Oxidation of trans-beta-Methylstyrene with NaOCl Catalyzed by $Ni^{II}$ Complexes.[1,2] | | |
|---|---|---|---|
| catalyst | recovered starting material | epoxide | benzaldehyde |
| II (a) | 0 | 51 | 23 |
| II (b) | 49 | 26 | 9 |
| II (c) | 96 | 1 | 2 |
| II (d) | 87 | 2 | 6 |

[1]Yields based on initial alkene conc.; balance is sodium benzoate. [2]Reaction conditions: 1.7 mmol alkene, 0.04 mmol $Ni^{II}$ catalyst, 0.08 mmol $PhCH_2NMe_3^+Br^-$ in 5 mL $CH_2Cl_2$ and 10 mL 0.77M NaOCl in water at room temperature.

The rate of epoxidation is accelerated and epoxidation product yields are increased by lowering the pH of the aqueous phase. While at pH 12.5 epoxidation requires 4–5 hours for 20–40 turnovers of catalyst, when the pH is lowered below 12.5, over 20 turnovers to give epoxide can be achieved in 15 minutes.

Similarly, the addition of certain organic phase soluble weak organic acids such as salen or ortho- or parasalicylaldehydes increases the reaction rate. A combination of both lowering the pH and the addition of weak organic acid leads to an even higher reaction rate. In typical reaction conditions, a solution of 4 mmol alkene, 0.15 mmol benzyltributylammonium bromide and 0.001–0.1 mmol nickel catalyst in 10 mL $CH_2Cl_2$ are stirred at room temperature with 20 mL 0.77M NaOCl adjusted to pH 9.3 using a buffer such as borate buffer. In one set of experiments, Gas chromotography analysis gave the results listed in Table II:

TABLE II

Turnover Numbers and Selectivity of Alkene epoxidation at Lowered pH Using HOCl and Ni$^{II}$ Catalysts

| entry | catalyst (mol %)[a] | pH | salen mol %[b] | substrate | conv.[c] % | epoxide select.[d] % | epoxide turnover no. min$^{-1}$ |
|---|---|---|---|---|---|---|---|
| 1 | 1 (2.5) | 12.5 | 0 | norbornene | 94 | 32 | 0.040 |
| 2 | 1 (2.5) | 9.3 | 7.5 | norbornene | 100 | 23 | 1.8 |
| 3 | 1 (2.5) | 12.5 | 0 | E — PhCH = CHCH$_3$ | 100 | 89 | 0.15 |
| 4 | 1 (0.063) | 9.3 | 1.5 | E — PhCH = CHCH$_3$ | 100 | 60 | 192 |
| 5 | 1 (0.013) | 9.3 | 0.3 | E — PhCH = CHCH$_3$ | 100 | 27 | 432 |
| 6 | 1 (0.013)[e] | 9.3 | 0.3 | E — PhCH = CHCH$_3$ | 63 | 76 | 640 |
| 7 | 2 (1.0) | 12.5 | f | E — PhCH = CHCH$_3$ | 30 | 53 | 0.047 |
| 8 | 2 (1.0) | 9.3 | f | E — PhCH = CHCH$_3$ | 100 | 45 | 9.0 |
| 9 | 2 (2.5) | 12.5 | f | cyclohexene | 100 | 13 | 0.17 |
| 10 | 2 (2.5) | 9.3 | f | cyclohexene | 100 | 16 | 0.21 |

[a](Moles catalyst/moles alkene) × 100. [b](Moles additional salen/moles alkene) × 100. [c]Disappearance of alkene. [d]Epoxide/total products. [e]Slow addition of NaOCl at rate of 1 equiv. NaOCl per alkene equiv. per min. [f]Additives such as salicylaldehyde had a small effect on the reaction.
Catalyst 1 was Ni(salen) (structure 4).
Catalyst 2 was catalyst II(a).

As can be seen from Table II, entry 6, at pH 9.3 with the addition of salen and slow addition of OCl$^-$, an alkene substrate can be epoxidized at a rate of at least 640 turnovers in one minute.

The data from the epoxidations of Table II is summarized in FIG. 1 showing the effect of pH and additives on turnover rate of Ni$^{II}$(salen)-catalyzed epoxidation of styrene using 2.5 mol % catalyst. Curve (A) is at pH 12.5 with no additives. Curve (B) is at pH 12.5 with 7.5 mol % salen added. Curve (C) is at pH 9.3 (borate buffer) with no additives. Curve (D) is at pH 9.3 (borate buffer) with 7.5 mol % salen added.

Catalysts II (a–d) may be prepared in accordance with the method described below starting from L-phenylalanine, L-leucine, L-valine and glycine, respectively. This synthetic pathway preserves the stereochemistry of the alpha carbon atom of the amino acid, which ultimately becomes the carbon atom at the 3 and 9 position of the 14 member ring and at the 3 and 8 positions of the 13 member ring. When L$_1$ and L$_2$ groups and the groups on the double bond of the alkene are sufficiently bulky, asymmetric induction will occur, and the resulting epoxide is chiral. This is not the case, however, for trans-beta-methylstyrene and any of catalyst complexes II a–d. No asymmetric induction occurred during these reactions under the conditions described above. (Catalyst IId is also commercially available from Aldrich Chemical Company.)

The most efficient catalysis occurred in the presence of IIa derived from phenylalanine. After 6.5 hours, all of the alkene was consumed, and two types of reaction products were formed. About half of the methylstyrene was converted to the corresponding epoxide. The other half of the methylstyrene underwent C=C bond cleavage to produce benzaldehyde and, presumably, acetaldehyde, which was not detected under the conditions of analysis. Since benzaldehyde is slowly oxidized by basic hypochlorite to water-soluble benzoate, analysis of the CH$_2$Cl$_2$ layer provided reliable data only for the determination of disappearance of starting material and appearance of epoxide. Relative amounts of PhCHO and PhCO$_2$H were variable.

Synthesis of Compounds

Compounds IA and IB may be prepared by various methods. Scheme I shows a convenient and general synthesis for forming IIa, which is the nickel complex of structure IA wherein m and n represent 1; X$_1$ and X$_2$ represent oxygen; Y$_1$, Y$_2$, Y$_3$ and Y$_4$ represent hydrogen; Z$_1$ and Z$_2$ represent two single bonded hydrogen atoms and L$_1$ and L$_2$ represent benzyl. The starting material in Scheme I is phenylalanine.

In the first step of Scheme I, the amino group of phenylalanine is protected with a protecting group, and the carboxyl group is activated by conversion to an ester (III). Some examples of protecting groups include, for example, carbobenzyloxy (cbz) and tertiary-butyloxycarbonyl (t-boc). Some examples of activated esters include, for example, the N-hydroxysuccinimide and aryl esters.

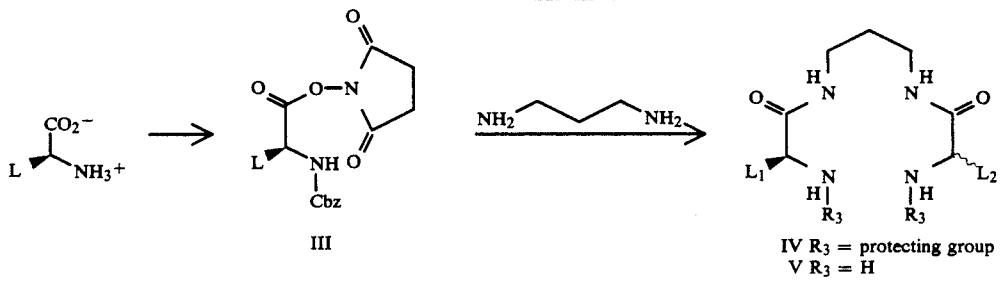

Scheme 1

Scheme 1 -continued

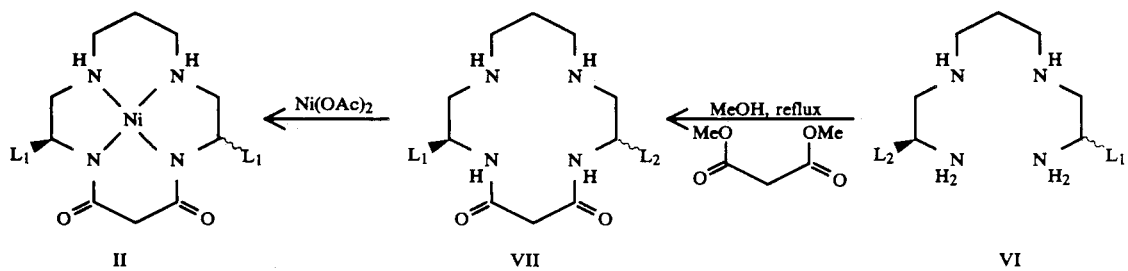

L = L₁ and L₂
a, L = CH₂Ph;b, L = CH₂CH(CH₃)₂;c, L = CH(CH₃)₂;d, L = H

Compound III is condensed with at least 0.5 equivalents of 1,3-diaminopropane in a suitable solvent to form protected diamide IV. Some suitable solvents include, for example, DME, DMF, THF, and dioxane. The carbobenzyloxy group is removed by catalytic hydrogenolysis with, for example, palladium on activated carbon in a suitable solvent such as, for example, acetic acid, methyl alcohol or ethyl alcohol, or by hydrolysis with HF, HCl, or HBr.

The resulting diamide V is reduced to tetraamine VI. Some suitable reducing agents for converting diamide V to tetraamine VI include, for example, borane/THF, and lithium aluminum hydride.

Tetraamine VI is treated with dimethyl or diethyl malonate or malonyl dichloride under suitable conditions, such as, for example, refluxing methyl alcohol for five days to form dioxocyclam VII.

It is readily apparent that Scheme I may be modified in order to produce other compounds of IA and IB. For example, compounds wherein $Z_1$ and $Z_2$ represent two singly bonded hydrogen atoms may be prepared by eliminating the step in which diamide V is reduced to tetraamine VI. Compounds wherein m represents 0 may be prepared by treating diamine VI with dimethyl oxalate or oxalyl dichloride. Compounds where n represents 0 may be prepared by treating ester III with 1,2-diaminoethane instead of 1,3-diaminopropane. Compounds wherein $X_1$ and $X_2$ both represent two singly bonded hydrogen atoms may be prepared by reduction of diamide VII with, for example, borane/THF. Compounds wherein $Y_1$ and $Y_2$ independently represent lower alkyl or carboxymethyl may be prepared by starting with one or more amino acids wherein the amino group is substituted with an alkyl or carboxymethyl group.

Alternatively, $Y_1$, $Y_2$, $Y_3$ and/or $Y_4$ that represent H and are on an amino, as opposed to an amido, nitrogen atom may be converted to $Y_1$, $Y_2$, $Y_3$ and/or $Y_4$ that represent lower alkyl or carboxymethyl by treatment with an appropriate alkylating agent such as, for example, an alkyl halide, especially an alkyl bromide or iodide, or a haloacetic acid, especially bromoacetic acid. Approriate protecting groups may be employed where required.

Compounds wherein $Y_3$ and $Y_4$ represent lower alkyl or carboxymethyl groups may be prepared by treating ester III with 1,3-diaminopropane wherein the amino groups are substituted with a lower alkyl or carboxymethyl group. Compounds having configurations other than the SS configuration at carbon atoms 3 and 9 of compound IA wherein m and n represent 1 and positions 3 and 8 wherein m represents 0 and n represents 1 may be prepared by starting with amino acids having the D (i.e. R) configuration.

The tetraamide and tetraamine intermediates obtained prior to forming the macrocyclic ring with oxalic or maleic acid derivatives (i.e., IV, V and VI) are useful not only as intermediates for forming the macrocyclic compounds of the present invention, but also as transition metal ion complexing agents. These compounds may be generally represented as follows:

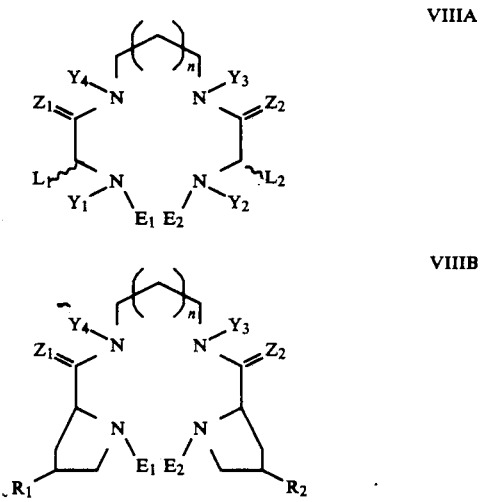

wherein $Y_1$, $Y_2$, $L_1$, $L_2$, $Z_1$, $Z_2$, $Y_3$, $Y_4$, $R_1$, $R_2$, and n all have the meanings described above and $E_1$ and $E_2$ represent H or a protecting group.

EXAMPLES

General Procedure for N-carbobenzyloxy-L-amino acid N-hydroxysuccinimide esters (III). L-alpha-amino acids were converted to their Cbz analogs according to prior art procedures (Ramage et al., J. Chem. Soc., Perkin 1, 461–470 (1985)). These products were then treated with N-hydroxysuccinimide by known procedures to produce compound III (Anderson et al., J. Am. Chem. Soc., 86, 1839–1842 (1964)).

N,N'-Bis-(N-carbobenzyloxy-L-phenylalanyl)-1,3-diaminopropane (IVa). Compound IIIa (2.52 g, 6.40 mmol) was dissolved in anhydrous dimethyoxyethane (DME) (100 mL), cooled to 0° in an ice bath, and 1,3-diaminopropane (0.27 mL, 3.20 mmol) was added dropwise. The reaction mixture was allowed to warm to room temperature for 18 hours. The white precipitate that formed was collected to vacuum filtration, and the solid material was washed with small portions of cold H₂O followed by cold MeOH. The final product was stored in a vacuum desiccator containing P₂O₅. Yield, 198 g (98%); mp 226°–227° C.

N,N'-Bis-(N-carbobenzyloxy-L-leucyl)-1,3-diaminopropane (IVb). In a procedure similar to that described above for the synthesis of IVa, IIIb (11.60 g, 0.032 mol) was treated with 1,3-diaminopropane (1.19 g, 0.016 mol) to yield IVb as a white solid which was recrystallized from methanol to produce fine white crystals. Yield 8.01 g (88%); mp 177°–178° C.

N,N'-Bis-(N-carbobenzyloxy-L-valyl)-1,3-diaminopropane (IVC). In a procedure similar to that described for IVa, IIIc (16.51 g, 0.047 mol) was treated with 1,3-diaminopropane (1.74 g, 0.024 mol) to yield IVc as a white solid recrystallized from isopropanol. Yield, 10.62 g (83%); mp 211°–212° C.

N,N'-Bis(phenylalanyl)-1,3-diaminopropane (Va).

Compound IVa (3.00 g, 4.72 mmol) was suspended in 200 mL MeOH. 5% Pd on activated carbon (0.35 g) was added and the mixture was degassed (by successive evacuation and venting to hydrogen) and treated with H₂(40 PSI) for 15 hours. The resulting solution was filtered through celite, washed several times with MeOH and concentrated to give a clear colorless oil. Trituration with diethylether resulted in the formation of IVa as a white solid.

N,N'-Bis-(leucyl)-1,3-diaminopropane (Vb). In a procedure similar to that described for Va, compound IVb (3.07 g, 5.40 mmol) was subjected to hydrogenolysis to produce Vb as a slightly yellow semi-solid. Yield 1.60 g (98.6%).

N,N'-Bis-(valyl)-1,3-diaminopropane (Vc). In a procedure analogous to that described for the preparation of Va, compound IVc (2.97 g, 5.50 mmol) was subjected to hydrogenolysis to produce Vc as a clear colorless oil. Yield, 1.46 g (98%).

(2S, 10S)-2,10-dibenzyl-1,4,8,11-tetraazaundecane tetrahydrochloride (VIa. 4HCl). A 1M BH₃/THF solution (67 ml, 0.067 mol) was added dropwise over a 1 hour period to a cooled (0° C.) solution of Va (4.1 g, 11.1 mmol) in anhydrous THF (100 mL). After addition was complete, the solution was allowed to warm to room temperature for 1 hour followed by heating to reflux for an additional 18 hours. The resulting solution was cooled, and the excess diborane was quenched by the dropwise addition of a 10% HSO/THF solution. The solvent was removed in vacuo, and 6M HCl (100 ml) was added to the residue and heated to reflux for 1 hour. After cooling, the solution was concentrated to a white semi-solid. A 4M NaOH solution (40 ml) was added, and the solution was extracted 4 times with 100 ml portions of CHCl₃. The organic layers were combined, dried (Na₂SO₄), filtered, and concentrated to give a yellow oil, which was subsequently dissolved in absolute EtOH (75 ml). HCl gas was passed through the EtOH solution. The resulting white precipitate that formed was collected by vacuum filtration and washed with cold EtOH. Yield, 5.3 g (83%), mp 243°–245° C. (dec.).

(2S, 10S)-2,10-di(iso-butyl)-1,4,8,11-tetraazaundecane tetrahydrochloride (VIb 4HCl). In a procedure similar to that described above, compound Vb (1.44 g, 5.30 mmol) was treated with 6 equiv. BH₃/THF. After the normal work-up, the tetrahydrochloride salt of VIb was isolated as a white powder. Yield, 2.08 g (93%).

(2S, 10S)-2,10-diisopropyl-1,4,8,11-tetraazaundecane tetrahydrochloride (VIc 4HCl). In a procedure similar to that described above, compound Vc (1.40 g, 5.14 mmol) was treated with 6 equiv. BH₃/THF. The normal work-up produced the tetrahydrochloride salt of VIc as a white solid. Yield, 1.50 g (75%), mp>260° C.

(3S, 9S)-3,9-Dibenzyl-1,4,8,11-tetraazacyclotetradecane-5,7-dione (VIIa)). Compound VI(a) (1.02 g, 2.90 mmol) and dimethyl malonate (0.47 g, 2.90 mmol) were heated at reflux in anhydrous MeOH (100 mL) for 5 days. After cooling, the reaction mixture was concentrated to a yellow oil which was then triturated with diethyl ether, resulting in the formation of an off-white solid. Further purification of the solid material by column chromatography on silica gel (15% MeOH/CHCl₃) led to the isolation of VII(a) as a white solid. Yield, 70.8 mg, (8%) mp 235°–237° C. (dec).

(3S, 9S)-3,9-Dibenzyl-1,4,8,11-tetraazacyclotetradecane-5,7-dione]nickel$^{II}$ (IC(b). Following the general procedure given for VII(a), compound VI(b) (39.8 mg, 0.117 mmol) was treated with Ni(OAc)₂ (30 mg, 0.12 mmol) to give the yellow complex IIb. Yield, 32 mg (70%).

(3S, 9S)-3,9-isopropyl-1,4,8,11-tetraazacyclotetradecane-5,7-dione]nickel$^{II}$ (IC(c)). Following the general procedure described for IIb, compound ID(c) (32 mg, 0.102 mmol) was treated with Ni(OAc)₂ (25 mg, 0.100 mmol) to give IIc as a yellow solid. Yield, 33 mg, (88%).

General Procedure For First Oxidation Studies

In a typical experiment 1.7 mmol trans-beta-methylstyrene, 0.04 mmol of the appropriate Ni$^{II}$ catalyst (IIa–d) and 0.08 mmol PhCH₂NME₃$^{+Br-}$(phase transfer catalyst) were dissolved in 5 mL CH₂Cl₂ and stirred vigorously with 10 mL 0.77 M aqueous NaOCl (pH 12–13). Aliquots of the organic layer were periodically removed, passed through a short column of neutral alumina, and analyzed for oxidation products by gas chromatography using a 5% phenyl methyl silicone capillary column (10 m×0.53 mm) with PhBr as an internal standard.

General Procedure For Second Oxidation Studies: Epoxidation with Controlled pH

Norbornene, trans-B-methylstyrene and cyclohexene were individually reacted in a solution of 4 mmol alkene, 0.15 mmol benzyltributylammonium bromide as a phase transfer catalyst and 0.001–0.1 mmol nickel salen or nickel dioxocyclam catalyst in 10 mL CH₂Cl₂. The mixture was stirred at room temperature with 20 mL 0.77M NaOCl at pH 12.5 or adjusted to pH 9.3 with borate buffer. In test mixtures 2, 4, 5 and 6 additional salen was added in amounts of 7.5, 1.5, 0.3 or 0.3 respectively mole percent per mole of alkene substrate. Salicylaldehyde was added to test mixtures 7, 8, 9 and 10. In test mixture 6, NaOCl was slowly added at a rate of 1 equiv. NaOCl per alkene equivalent per minute. Gas chromatography analysis was undertaken using a dichlorobenzene as an internal standard. The results are shown above in Table II.

Epoxidation Control Studies

Control studies were carried out to insure that the reaction is metal-dependent, independent of other oxidants such as O₂, and that the epoxidation occurs only in the organic phase. In a transport-type experiment, two CH₂Cl₂ solutions containing alkene and phase transfer catalyst were connected by an aqueous NaOCl solution. Epoxidation occurred only in one CH₂Cl₂ solution which also contained Ni$^{II}$(salen).

In another experiment, Alkene and Ni$^{II}$ (salen) were added to a solution of anhydrous Bu₄N⁺OCl⁻ in CH₂Cl₂. No epoxide was formed after 30 min.; however, additional of excess benzoic acid led to 26 turnovers of epoxide. It was concluded that HOCl rather than OCl⁻ is the reactive oxidation with Ni$^{II}$ catalyst.

While there have been described what are presently believed to be the preferred embodiments of the invention, those skilled in the art will realize that changes and modifications may be made thereto without departing from the spirit of the invention and it is intended to claim all such changes and modifications as falling within the true scope of the invention.

What is claimed is:

1. A 13 or 14 member macrocyclic compound having the following ring nucleus:

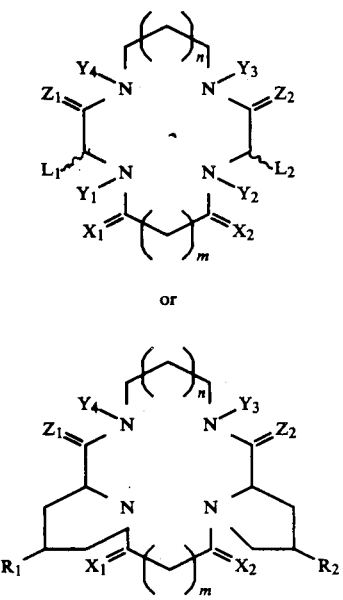

wherein:
n=0 or 1;
m=0 or 1;
n+m>0;
X₁, X₂, Z₁, and Z₂ independently represent H₂ or 0 except that X₁, X₂, Z₁, and Z₂ do not all represent H₂; and
Y₁, Y₂, Y₃, and Y₄ independently represent H, lower alkyl or CH₂COOH; and
L₁ and L₂ independently represent side chains of alpha amino acids, except that L₁ and L₂ do not both represent H; and
R₁ and R₂ independently represent H or OH; and
two carbon atoms, one bearing L₁ and another bearing L₂, have a configuration wherein both of the two carbon atoms have the S configuration, or both of the two carbon atoms have the R configuration, or one of the two carbon atoms has the S configuration while the other has the R configuration.

2. The compound of claim 1 wherein the carbon atom bearing L₁ and the carbon atom bearing L₂ have the S configuration.

3. The compound of claim 1 wherein the carbon atom bearing L₁ an the carbon atom bearing L₂ have the R configuration.

4. The compound of claim 1 wherein one of the carbon atoms bearing L₁ or L₂ has the S configuration and the other carbon atom bearing L₁ or L₂ has the R configuration.

5. The compound of claim 1 wherein Z₁ and Z₂ each represent two singly bonded hydrogen atoms.

6. The compound of claim 1 wherein X₁, X₂, Z₁ and Z₂ represent 0.

7. The compound of claim 1 wherein X₁ and X₂ represent 0 and Z₁ and Z₂ represent H₂.

8. The compound of claim 1 wherein X₁ and X₂ represent H₂ and Z₁ and Z₂ represent 0.

9. The compound of claim 7 wherein Y₁ and Y₂ represent H and Y₃ and Y₄ represent CH₂CO₂H.

10. The compound of claim 8 wherein Y₁ and Y₂ represent CH₂CO₂H and Y₃ and Y₄ represent H.

11. The compound of claim 1 wherein n+m=2.

12. The compound of claim 1 wherein n+m=1.

13. A complex of a transition metal ion and a 13 or 14 member macrocyclic ring compound having the following ring nucleus:

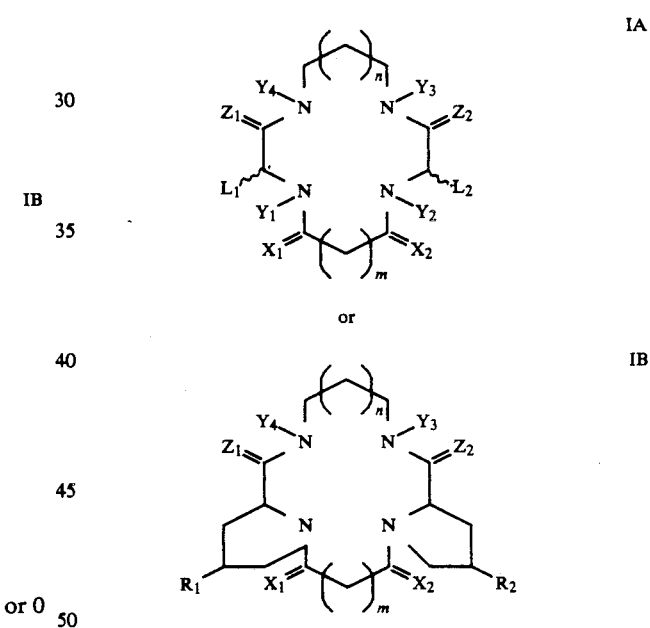

wherein:
n=0 or 1;
m=0 or 1;
n+m>0;
X₁, X₂, Z₁, and Z₂ independently represent H₂ or 0; and
Y₁, Y₂, Y₃, and Y₄ independently represent H, lower alkyl or CH₂COOH; and
L₁ and L₂ independently represent side chains of alpha amino acids, except that L₁ and L₂ do not both represent H; and
R₁ and R₂ independently represent H or OH; and
two carbon atoms, one bearing L₁ and another bearing L₂, have a configuration wherein both of the two carbon atoms have the S configuration, or both of the two carbon atoms have the R configuration, or one of the two carbon atoms has the S configuration while the other has the R configuration.

14. The complex of claim 13 wherein the carbon atom bearing $L_1$ and the carbon atom bearing $L_2$ have the S configuration.

15. The complex of claim 13 wherein the carbon atom bearing $L_1$ and the carbon atom bearing $L_2$ have the R configuration.

16. The complex of claim 13 wherein one of the carbon atoms bearing $L_1$ or $L_2$ has the S configuration and the other carbon atom bearing $L_1$ or $L_2$ has the R configuration.

17. The complex of claim 13 wherein $X_1$, $X_2$, $Z_1$ and $Z_2$ represent $H_2$.

18. The complex of claim 13 wherein $X_1$, $X_2$, $Z_1$ and $Z_2$ represent 0.

19. The complex of claim 13 wherein $X_1$ and $X_2$ represent 0 and $Z_1$ and $Z_2$ represent $H_2$.

20. The complex of claim 13 wherein $X_1$ and $X_2$ represent $H_2$ and $Z_1$ and $Z_2$ represent 0.

21. The complex of claim 19 wherein $Y_1$ and $Y_2$ represent H and $Y_3$ and $Y_4$ represent $CH_2CO_2H$.

22. The complex of claim 20 wherein $Y_1$ and $Y_2$ represent $CH_2CO_2H$ and $Y_3$ and $Y_4$ represent H.

23. The complex of claim 13 wherein the metal is a member of the first transition series, the second transition series, the lanthanide series or the third transition series.

24. The complex of claim 13 wherein the metal ion is $Ni^{2+}$, $Co^{2+}$, $Cu^{2+}$, $Mn^{2+}$, and $Gd^{3+}$ $Pt^{2+}$ and $Pd^{2+}$.

25. The complex of claim 13 wherein the metal ion is $Ni^{2+}$.

* * * * *

UNITED STATES PATENT AND TRADEMARK OFFICE
CERTIFICATE OF CORRECTION

PATENT NO. : 4,987,227  Page 1 of 1
DATED : January 22, 1991
INVENTOR(S) : Burrows et al.

It is certified that error appears in the above-identified patent and that said Letters Patent is hereby corrected as shown below:

Title page,
Item [75], Inventors, please delete "Heungsik Yoon, both of",
Item [57], ABSTRACT,
Line 21, "a ph about" should read -- a pH from about --.

Drawings,
"12 Drawing Sheets" should read -- 1 Drawing Sheet --.

Column 15,
Line 59, "Approriate" should read -- Appropriate --.

Column 19,
Line 8, "oxidation" should read -- oxidant --.

Column 20
Line 2, "an" should read -- and --.
Lines 12-16, "0" should read -- O --.

Column 21,
Lines 16-17, "0" should read -- O --.

Column 22,
Lines 1-4, "0" should read -- O --.

Signed and Sealed this

Sixth Day of August, 2002

Attest:

JAMES E. ROGAN
Attesting Officer    Director of the United States Patent and Trademark Office